(12) United States Patent
Percival et al.

(10) Patent No.: US 6,623,429 B2
(45) Date of Patent: Sep. 23, 2003

(54) HAND-HELD NON-CONTACT TONOMETER

(75) Inventors: Christopher J. Percival, Williamsville, NY (US); Douglas H. Hoover, Corfu, NY (US); David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 7 days.

(21) Appl. No.: 09/992,875

(22) Filed: Nov. 6, 2001

(65) Prior Publication Data

US 2003/0088169 A1 May 8, 2003

(51) Int. Cl.[7] .................................................. A61B 3/16
(52) U.S. Cl. ........................................ 600/399; 600/561
(58) Field of Search ................................ 600/398, 399, 600/401, 405, 561, 587; 351/205, 208

(56) References Cited

U.S. PATENT DOCUMENTS

| | | | |
|---|---|---|---|
| 3,585,849 A | 6/1971 | Grolman et al. | 600/401 |
| 4,724,843 A | 2/1988 | Fisher | 600/401 |
| 4,747,296 A | 5/1988 | Feldon et al. | 73/1.62 |
| 4,817,620 A * | 4/1989 | Katsuragi et al. | 600/401 |
| 5,446,274 A * | 8/1995 | Luce et al. | 250/206.2 |
| 5,565,939 A * | 10/1996 | Fujieda | 351/212 |
| 5,629,747 A * | 5/1997 | Miyake | 351/218 |
| 5,865,742 A * | 2/1999 | Massie | 600/405 |
| 6,361,495 B1 * | 3/2002 | Grolman | 600/401 |
| D468,430 S * | 1/2003 | Hoelbl | D24/172 |

FOREIGN PATENT DOCUMENTS

EP 1 121 895 A2 8/2001

* cited by examiner

*Primary Examiner*—Max F. Hindenburg
*Assistant Examiner*—Charles A. Marmor, II
(74) *Attorney, Agent, or Firm*—Hodgson Russ LLP

(57) ABSTRACT

A hand-held non-contact tonometer comprises a housing having a handle portion for enclosing a rechargeable D.C. power source and an upper head portion for enclosing alignment and tonometric measurement systems of the tonometer. An operator can directly view the patient's eye along an optical axis extending through the head portion of the housing, and an instructional display image is superimposed with the directly viewed image of the eye to guide the operator in X-Y-Z alignment based on data supplied by an afocal position detection system. A transceiver for wireless data exchange and a recharging support stand are also provided.

11 Claims, 10 Drawing Sheets

HAND-HELD NON-CONTACT TONOMETER

BACKGROUND OF THE INVENTION

I. Field of the Invention

The present invention relates generally to ophthalmic instruments, and more particularly to a portable hand-held non-contact tonometer for measuring intraocular pressure of a patient's eye.

II. Description of the Related Art

Non-contact tonometers are diagnostic instruments widely used by ophthalmologists and medical personnel for measuring the internal fluid pressure within the eye (intraocular pressure or IOP), often to screen patients for elevated IOP associated with glaucoma. Non-contact tonometers typically operate by directing a fluid pulse at the eye and observing deformation of the cornea. In conventional apparatus of the prior art, a fluid pump having a solenoid-driven piston compresses fluid within a plenum chamber, and a fluid discharge tube in communication with the plenum chamber and aligned with the patient's eye delivers a fluid pulse to the eye that deforms the cornea from its normal convex state, through a flattened state known as "applanation," to a concave state. When the fluid pulse dissipates, the cornea returns to its normal convex state. The deformation is monitored by opto-electronic means, and a quantity such as the plenum pressure at the moment of applanation or the time required to achieve applanation is measured and correlated to IOP.

Heretofore, non-contact tonometers have been primarily bulky "table top" instruments that are not easily portable. In practice, the patient sits at one end of the instrument with his or her head steadied by a forehead brace, and the operator sits at the opposite end to align the instrument relative to the eye and administer the test. The instrument, which contains precisely aligned optical components, remains stationary on the table except for a test portion that moves relative to a base of the instrument for alignment purposes.

The desirability of a smaller, lightweight instrument for measuring IOP has been recognized for some time, as evidenced by the development of hand-held "contact" type tonometers. See for example, U.S. Pat. Nos. 4,192,317; 4,622,459; 4,747,296; and 5,174,292. Because a portion of the tonometer physically contacts the cornea, these instruments are generally regarded as being less comfortable to the patient than the non-contact variety described above, and there is an increased risk of infection because viruses and bacteria can be transferred from one patient to the next. Moreover, an operator's skill in testing can have a significant impact upon measurement results, thus rendering these instruments poorly suited for use by general medical practitioners.

U.S. Pat. No. 4,724,843 describes a portable non-contact tonometer that includes a carrying case 102 for housing a pump used to generate a fluid pulse, and a detachable hand-held unit 100 connected to the pump by a flexible connection line 104 enclosing a fluid conduit. Thus, only a portion of the instrument is hand-held, with the remainder of the instrument being large and heavy. The non-contact tonometer described in U.S. Pat. No. 4,724,843 is complex and expensive to manufacture.

BRIEF SUMMARY OF THE INVENTION

Therefore, it is an object of the present invention to provide a non-contact tonometer that is designed for hand-held use.

It is another object of the present invention to provide a non-contact tonometer that is compact and lightweight for easy transport.

It is yet another object of the present invention to provide a non-contact tonometer that is battery powered to avoid the use of power cords.

It is yet another object of the present invention to provide a compact handheld non-contact tonometer that is designed so as to reduce the risk of damage to internal components thereof.

It is yet another object of the present invention to provide a hand-held non-contact tonometer having a fast position detection system for facilitating hand-operated alignment of the tonometer.

It is yet another object of the present invention to provide a non-contact tonometer that is equipped for wireless data communication with a remote computer to enable uploading of measurement data without need for communication cables.

In furtherance of these and other objects, a non-contact tonometer according to a preferred embodiment of the present invention includes a housing having a handle portion that encloses a rechargeable D.C. power source and an upper head portion that encloses alignment and tonometric measurement systems of the tonometer. The bottom of the handle portion defines a curved surface that prevents the instrument from being rested on the handle alone, because this would be a precarious state given the tonometer's high center of gravity and the fact that critical optical and opto-electronic elements are located within the head portion of the housing. A stand comprising a battery recharger is provided in combination with the tonometer for supporting the tonometer and recharging the tonometer's power source while the instrument is not in use.

An operator must position and align the tonometer by hand relative to a patient's eye. To assist the operator, an optical axis extends through the head portion from the patient end where a fluid discharge tube is located to the operator end where an eyepiece is located, and the operator is afforded a direct view of the eye without the use of a camera or the like. A fast afocal position detection system is also incorporated in the head portion for determining X-Y-Z alignment status of the tonometer relative to the patient's eye. The position detection system comprises first and second light sources on opposite sides of the optical axis, and corresponding first and second light-sensitive area detectors positioned to receive light from an associated light source after it has been reflected by the cornea. The detectors provide signal information indicative of the local x-y position of an illumination spot formed thereon. In the preferred embodiment, the first and second detectors are quad-cell detectors having four quadrants, and the illumination spot size is about the size of one quadrant, whereby the x-y position can be determined based on the four signal levels generated by the quadrants. Collector lenses after each light source and in front of each detector minimize vergence in the light beam as it illuminates the eye and as it arrives at a detector.

The local x-y data from each detector are then provided as input to a series of stored geometrical relationships determined during instrument calibration for giving the X-Y-Z global alignment status of the tonometer relative to the eye. The geometrical relationships are multiple regression equations for X, Y, and Z, wherein regression coefficients for each equation are determined by reading local x-y data from the detectors for an artificial eye placed at a plurality of known X-Y-Z positions during calibration. The regression coefficients are stored and used during normal instrument operation to quickly calculate X, Y and Z coordinates based on local x-y data from the detectors as an operator positions the instrument relative to a patient's eye.

A "heads-up" display is connected to receive the X-Y-Z position data and provide instructional cues to the operator for moving the instrument to achieve alignment. The heads-up display comprises a polar array of light emitting diodes selectively illuminated to indicate a desired X-Y movement direction, and a linear array of light emitting diodes selectively illuminated to indicate a desired Z movement direction. An image of the heads-up display is presented to the operator along the instrument optical axis through the use of a beamsplitter that allows the directly viewed image of the patient's eye to be transmitted as well along the optical axis, whereby the X-Y polar array is arranged circumferentially about the directly viewed image.

Tonometric measurement is carried out by generating a fluid pulse to deform the cornea, observing the occurrence of corneal applanation, and correlating a plenum pressure associated with the fluid pulse at the time of applanation with IOP. The tonometer thus includes a solenoid that is energized when the position detection system confirms alignment, a piston driven by the solenoid relative to a cylinder to generate a fluid pulse directed through the fluid discharge tube toward the patient's eye, a pressure sensor for monitoring plenum pressure, and an applanation emitter and applanation detector on opposite sides of the optical axis for observing applanation based on corneally reflected light.

The tonometer further comprises an IRDA infrared data association (IRDA) transceiver for wireless uploading of measurement data to a remote computer.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

General Configuration

Figure 1:
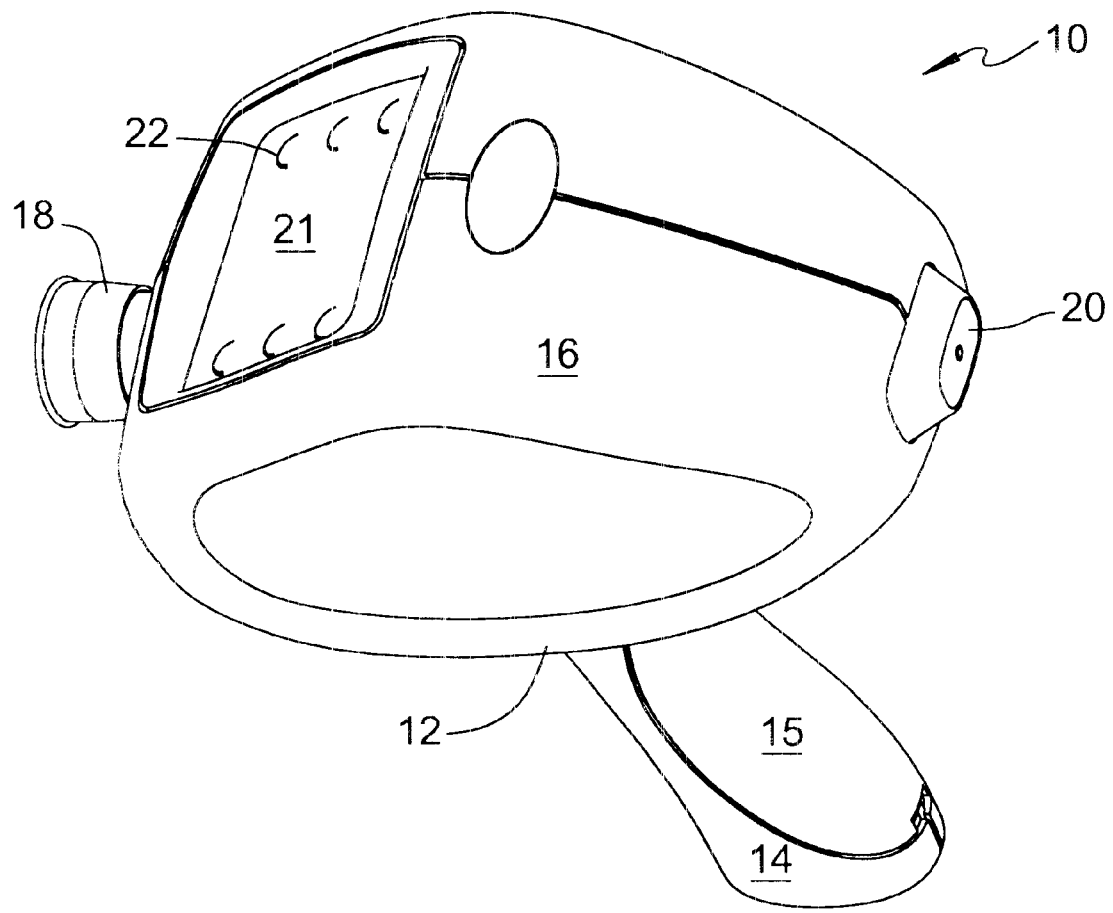
FIG. 1 is a perspective view of a hand-held non-contact tonometer formed in accordance with a preferred embodiment of the present invention.

FIG. 1 shows a hand-held non-contact tonometer 10 formed in accordance with a preferred embodiment of the present invention. Tonometer 10 includes a housing 12 characterized by an elongated handle portion 14 and an upper head portion 16 connected to a top end of handle portion 14. Housing 12 is formed of two generally symmetrical halves joined along a vertical plane. Handle portion 14 includes an ergonomically designed hand grip 15. As will be described in greater detail below, head portion 16 contains a tonometric measurement system and handle portion 14 contains a power source for the tonometric measurement system. Also visible in FIG. 1 is an operator eyepiece 18 at one end of head portion 16, a front window 20 at an opposite end of head portion 16 facing a patient, and a liquid crystal display 21 with pushbutton control overlay 22 angled toward the operator near operator eyepiece 18.

Figure 2:
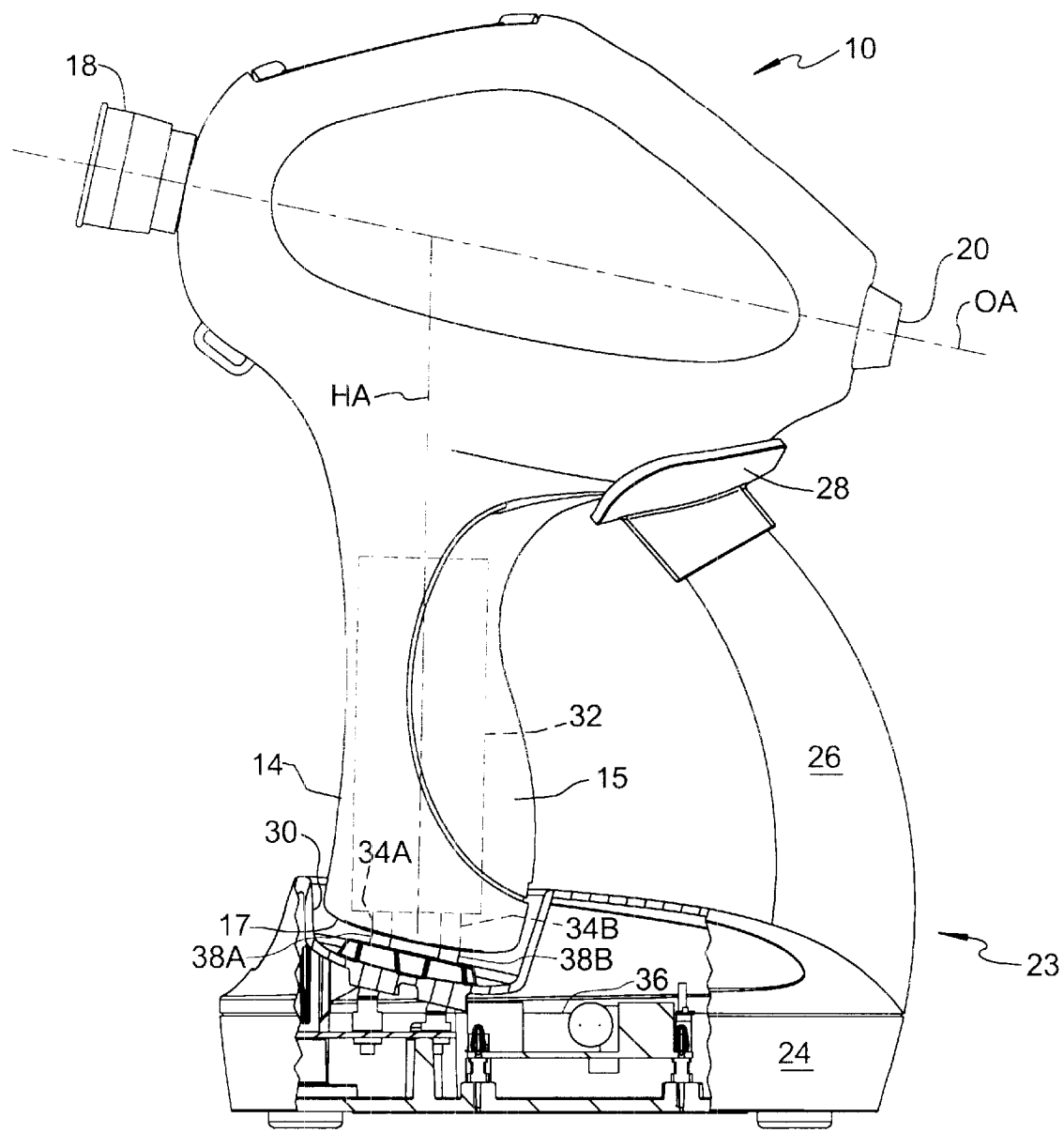
FIG. 2 is a side elevational view of the hand-held non-contact tonometer shown in FIG. 1, depicted resting in a support stand, partially sectioned, for receiving the non-contact tonometer when the non-contact tonometer is not in use.

FIG. 2 depicts tonometer 10 supported in an upright orientation by a stand 23. By "upright orientation" it is meant that handle portion 14 is below head portion 16. An optical axis OA extends through head portion 16 from operator eyepiece 18 through front window 20. It can be seen in FIG. 2 that a handle axis HA intersects optical axis OA at an oblique angle thereto, whereby tonometer 10 is more comfortably carried and positioned by an operator. Stand 23 includes a base 24, a generally arcuate support member 26 extending upwardly from base 24, and a saddle 28 fixed to support member 26 to receive and support head portion 16 and the components therein. A docking recess 30 is provided in base 24 for receiving a bottom end 17 of handle portion 14. Bottom end 17 is purposely formed to define a curved surface, such that tonometer 10 is not freestanding on its own, and this fact is readily apparent to an operator. Because head portion 16 of tonometer 10 includes critical optical components of the tonometric measurement and alignment systems discussed below, it is undesirable to have a freestanding instrument with such a high center of gravity which could easily be knocked over and potentially damaged.

Power Supply

The electronic components of tonometer 10 are powered by a D.C. power source 32 contained within handle portion 14. A suitable power source 32 is a rechargeable 3.7 Volt lithium ion battery manufactured by Panasonic under part no. CGR18650H. Power source 32 includes a pair of charging contacts 34A, 34B exposed through corresponding openings in the bottom end 17 of handle portion 14. Power source 32 is recharged when it is received and supported by stand 23. For this purpose, stand base 24 includes a battery charger 36 having charging contacts 38A, 38B exposed through openings in docking recess 30 for contact with charging contacts 34A, 34B of power source 32. A suitable battery charger is available from Condor D.C. Power Supplies, Inc. of Oxnard, Calif. under vendor part no. GSM7-12.

Figure 8:
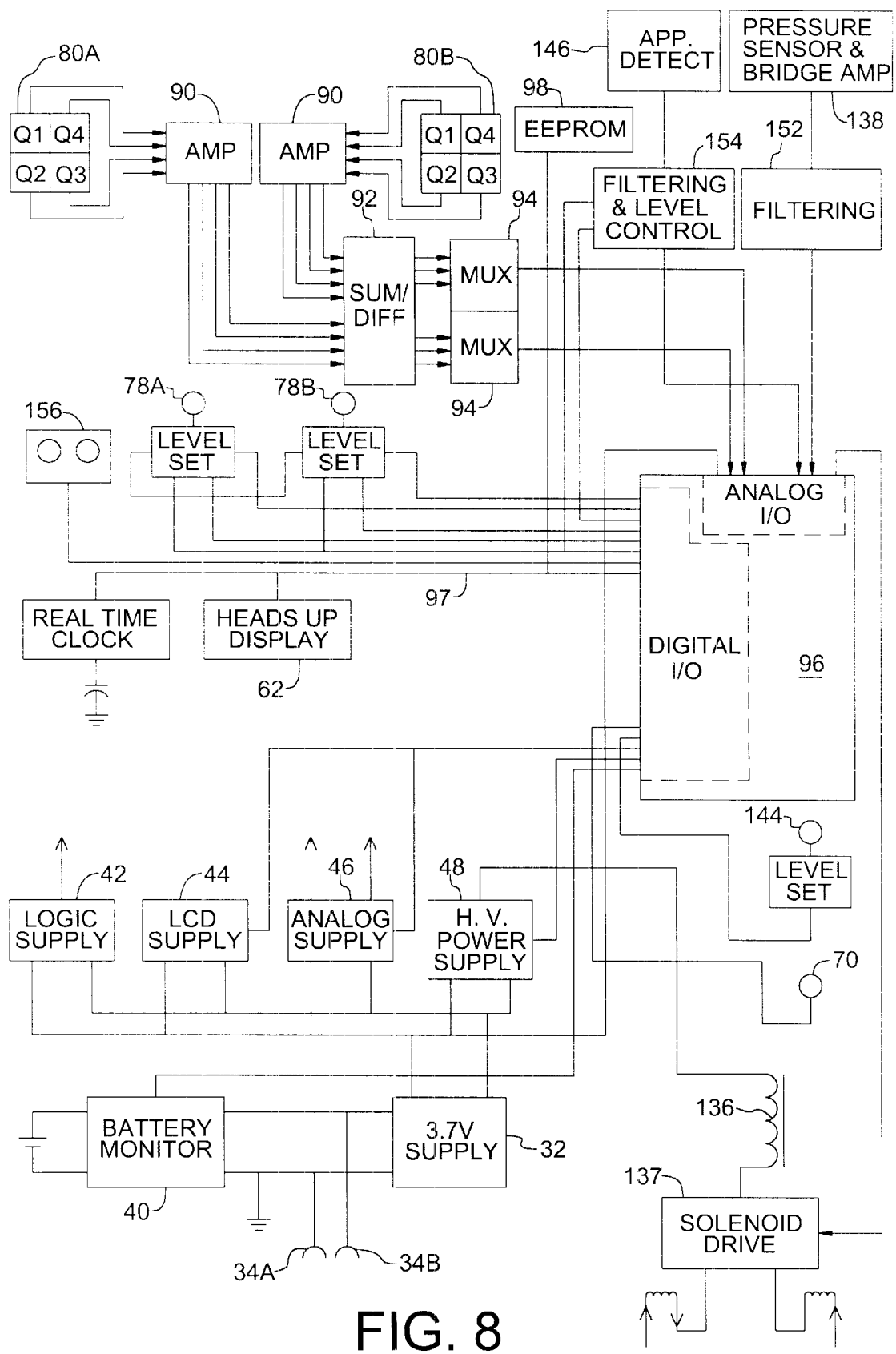
FIG. 8 is an electronic block diagram of the hand-held non-contact tonometer shown in FIG. 1.

Reference is now made to FIG. 8 of the drawings. Power source 32 is connected to a battery monitor circuit 40 that monitors the charge status of power source 32. Dedicated circuits are connected to main power supply 32 for supplying power to various systems of tonometer 10. These dedicated circuits include a logic supply circuit 42, an LCD supply circuit 44, an analog supply circuit 46, and a high-voltage power supply circuit 48.

Alignment System

Figure 3:
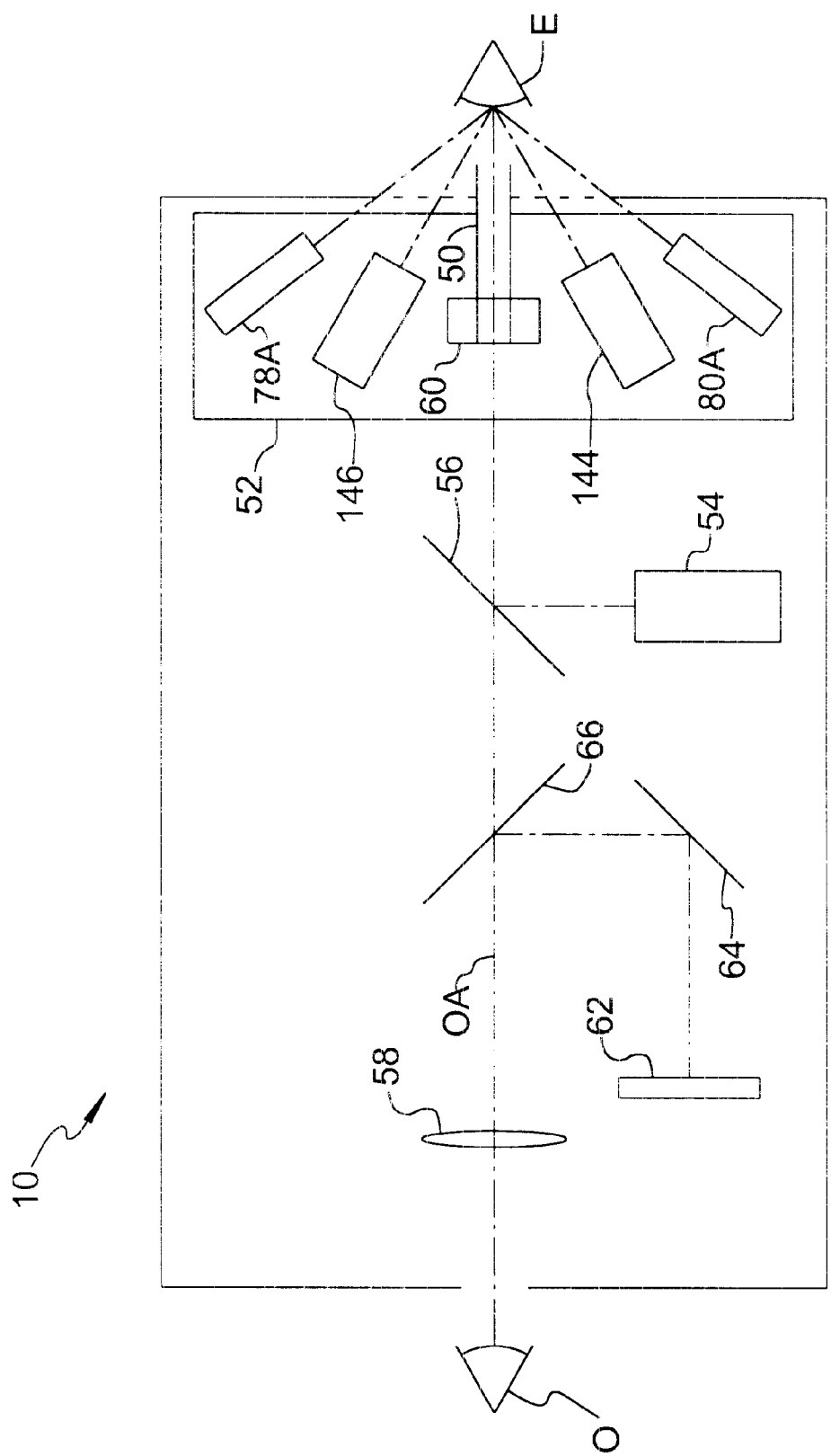
FIG. 3 is an optical schematic diagram of the hand-held non-contact tonometer shown in FIG. 1.

FIG. 3 is an optical schematic diagram of hand-held non-contact tonometer 10. Non-contact tonometer 10 is operable to discharge a fluid pulse through a fluid discharge tube 50 aligned along optical axis OA to cause observable deformation of a patient's cornea for purposes of measuring intraocular pressure. As a prerequisite to testing, it is necessary for an operator O to align the tonometer in three dimensions (X-Y-Z alignment) relative to a patient's eye E.

Tonometer 10 includes a nosepiece 52 fixed near a front section of head portion 16 for mounting various optical and opto-electronic elements of the tonometer as described below, a fixation target projecting system 54 cooperating with a beamsplitter 56 to present a visible fixation target to the patient along optical axis OA, an eyepiece lens 58 and a macro-lens 60 for enabling operator O to view the patient's eye E through the instrument along optical axis OA, a heads-up display 62, and a mirror 64 cooperating with a beamsplitter 66 to project an image of the heads-up display to the operator along optical axis OA. Macro-lens 60 is preferably a planar—planar lens such that the operator sees the eye in an unmagnified state, however it is possible to use a macro-lens having optical power to provide some other desired field of view and magnification with respect to the eye.

Figure 4:
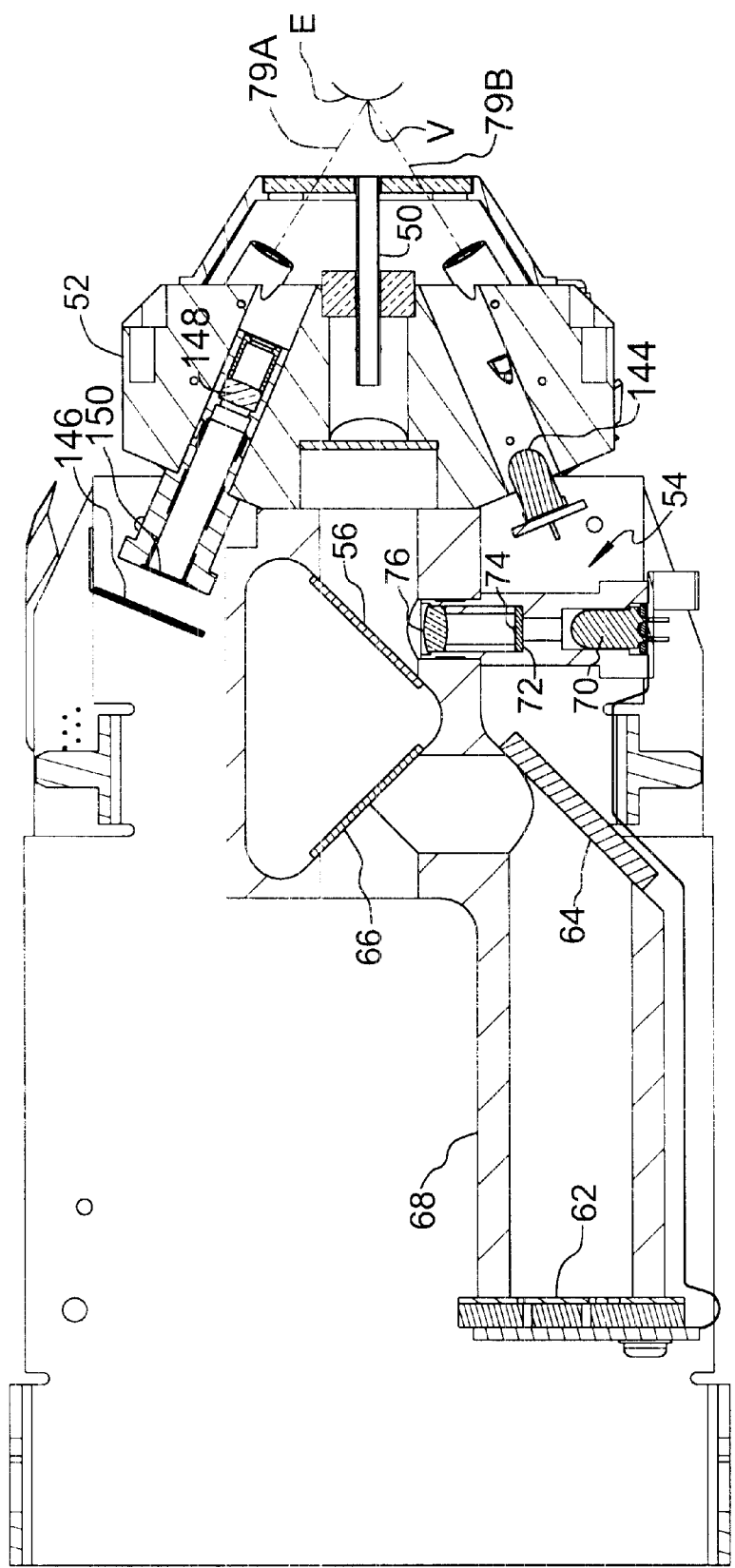
FIG. 4 is a sectional view of an optical block portion of the hand-held non-contact tonometer shown in FIG. 1.

FIG. 4 offers a sectional view of an optical block portion of tonometer 10 located within head portion 16 of housing 12. A mounting fixture 68 supports and positions heads-up display 62, mirror 64, beamsplitters 66 and 56, and elements of fixation target projecting system 54. FIG. 4 shows a preferred fixation target projecting system 54 in greater detail. An LED 70 emits light that passes through a finely ground diffuser element 72 having a central target dot 74 painted translucent red. The light from diffuser element 72 then passes through a collimating lens 76 before the collimated target light is reflected by beamsplitter 56 to follow optical axis OA. The use of a relatively dark target dot against a bright background field is preferred because the bright background light helps to illuminate the patient's eye E to aid the operator's direct view of the eye along optical axis OA. Additional light sources (not shown) mounted in or near nosepiece 52 may be employed to help illuminate eye E.

Attention is directed now to elements of a position detection system mounted in or on nosepiece 52. More specifically, the schematic representation of FIG. 3 shows a light source 78A on one side of optical axis GA and a detector 80A on an opposite side of optical axis GA used for position detection. In actual practice, nosepiece 52 supports a second light source 78B and a second detector 80B, which can be seen in the view of FIG. 5. In the embodiment described at present, light sources 78A and 78B are located just below the horizontal plane containing optical axis OA, while detectors 80A and 80B are located just above the horizontal plane containing optical axis GA, thereby leaving space in the horizontal plane for elements of an applanation detection system described below. First light source 78A directs a first beam of light along a first illumination axis 79A for illuminating eye E, and first detector 80A defines a first light-detecting area for receiving an image of first light source 78A formed by light reflected from the eye. Light traveling along first illumination axis 79A passes through a collector lens 82A and is obliquely incident to the generally spherical surface of the cornea, from which it is reflected toward first detector 80A. A collector lens 84A in front of first detector 80A substantially collimates the divergent beam coming from the generally spherical surface of the cornea, whereby a spot of illumination is received on the light-detecting area defined by first detector 80A. Essentially, first detector 80A detects an apparent or virtual source behind the cornea. Second light source 78W second illumination axis 79B, collector lenses 82B and 84B, and second detector 80B form a similar system, and are preferably arranged in opposing symmetry about the vertical plane containing optical axis GA. In a preferred construction, position light sources 78A and 78B are infrared light-emitting diodes for invisibility to the patient, and are Reply to Office Action of Jan. 13, 2003 mounted or formed on a single flexible circuit board to allow assembly of the tonometer with greater ease. Similarly, first and second detectors 80A, 80B are preferably carried by a flexible circuit board for easy assembly.

Figure 5:
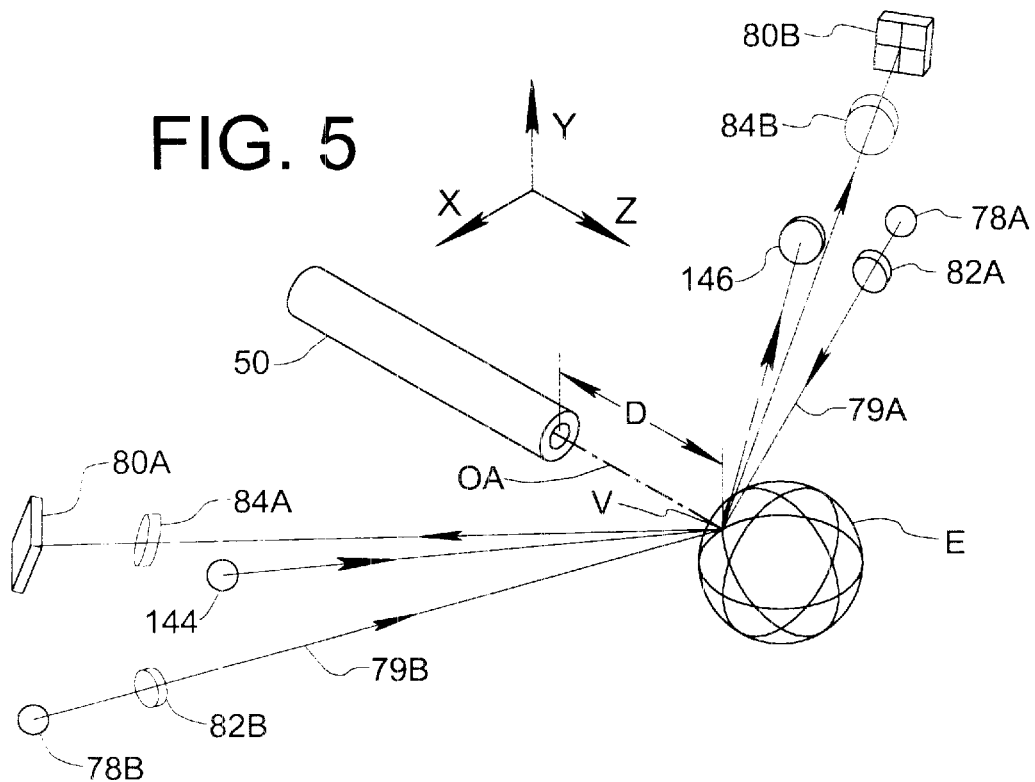
FIG. 5 is a schematic perspective view showing the arrangement of elements of a position detection system of the hand-held non-contact tonometer shown in FIG. 1.

In the illustration of FIG. 5, the instrument as represented by the exit end of fluid discharge tube 50 and the eye as represented by the corneal vertex V are shown in a state of three-dimensional (X-Y-Z) alignment. In the present embodiment, alignment is achieved when optical axis OA intersects and is normal to corneal vertex V, and the exit end of fluid discharge tube 50 is a predetermined firing distance D away from corneal vertex V in a Z-axis direction. The orientation of first detector 80A and that of second detector 80B are chosen such that the central ray of the corresponding corneally reflected illumination beam is normal to the light-detecting area of the associated detector and arrives substantially at a central point of the light-detecting area when X-Y-Z alignment exists.

Figure 6:
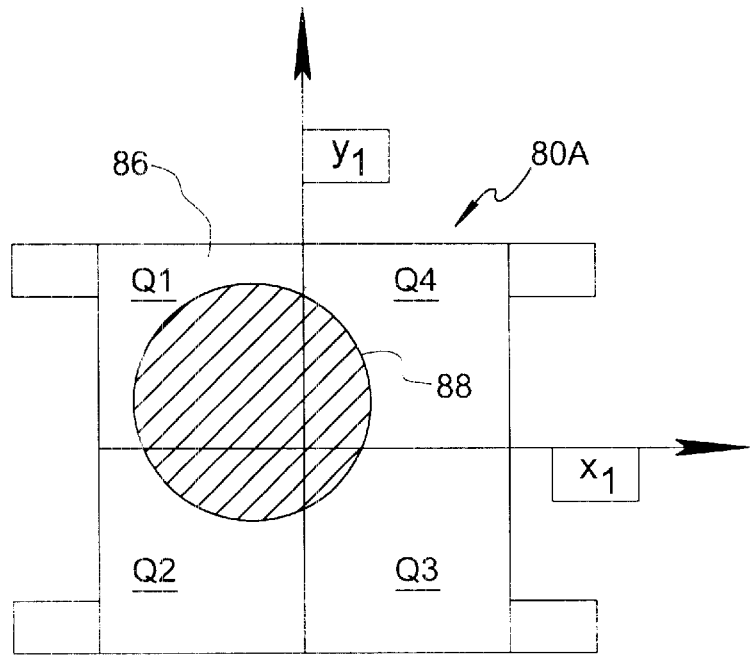
FIG. 6 is a detail view of a quad-cell detector of the position detection system shown in FIG. 5.

FIG. 6 shows a light-detecting area 86 of first detector 80A, with the understanding that the accompanying description also applies as well to second detector 80B. An image of light source 78A appears as a spot 88 on light detecting area 86. In the present embodiment, first detector 80A is a quad-cell detector comprising four quadrants Q1, Q2, Q3, and Q4 each providing a signal proportional to the illumination optical power received thereby. The size of each quadrant is preferably on the order of about 1.3 mm×1.3 mm, with a separation distance of about 0.1 mm between adjacent quadrant edges. The size of illumination spot 88 should be on the order of the size of one quadrant for meaningful x-y resolution. The size of illumination spot 88 will change during Z-axis adjustment as tonometer 10 is moved closer to or farther away from the eye. Moreover, the rate of change in spot size increases as the instrument moves closer to the eye. Therefore, it is desirable to optimize the system for a range of Z-axis positions centered about the predetermined firing distance D (i.e. +/−2.00 mm) such that the change in spot size for Z-axis positions throughout the range is minimized. Optimization can be carried out by selecting an appropriate front focal length for collector lenses 84A, 84B that causes the light striking detectors 80A, 80B to transition from being slightly convergent to being slightly divergent as the instrument is moved through the range of Z-axis positions toward the eye, wherein the light striking detectors 80A, 80B are approximately collimated when the instrument is at the predetermined firing distance D. In practice, it has been found that the firing distance D should be just beyond the front focal length of collector lenses 84A, 84B.

As will be understood, the signals from quadrants Q1–Q4 of first detector 80A are indicative of the local two-dimensional location $(x_1, y_1)$ of the centroid of spot image 88 in light detecting area 86, and the signals from quadrants Q1–Q4 of second detector 80B are indicative of the local two-dimensional location $(x_2, y_2)$ of a similar spot formed on the light detecting area of the second detector. The local x position is given by comparing the signal strengths from each quadrant as follows:

$$x=(Q3+Q4-Q1-Q2)/(Q1+Q2+Q3+Q4).$$

Likewise, the local y position is given by comparing the signal strengths from each quadrant as follows:

$$y=(Q1+Q4-Q2-Q3)/(Q1+Q2+Q3+Q4).$$

Figure 7:
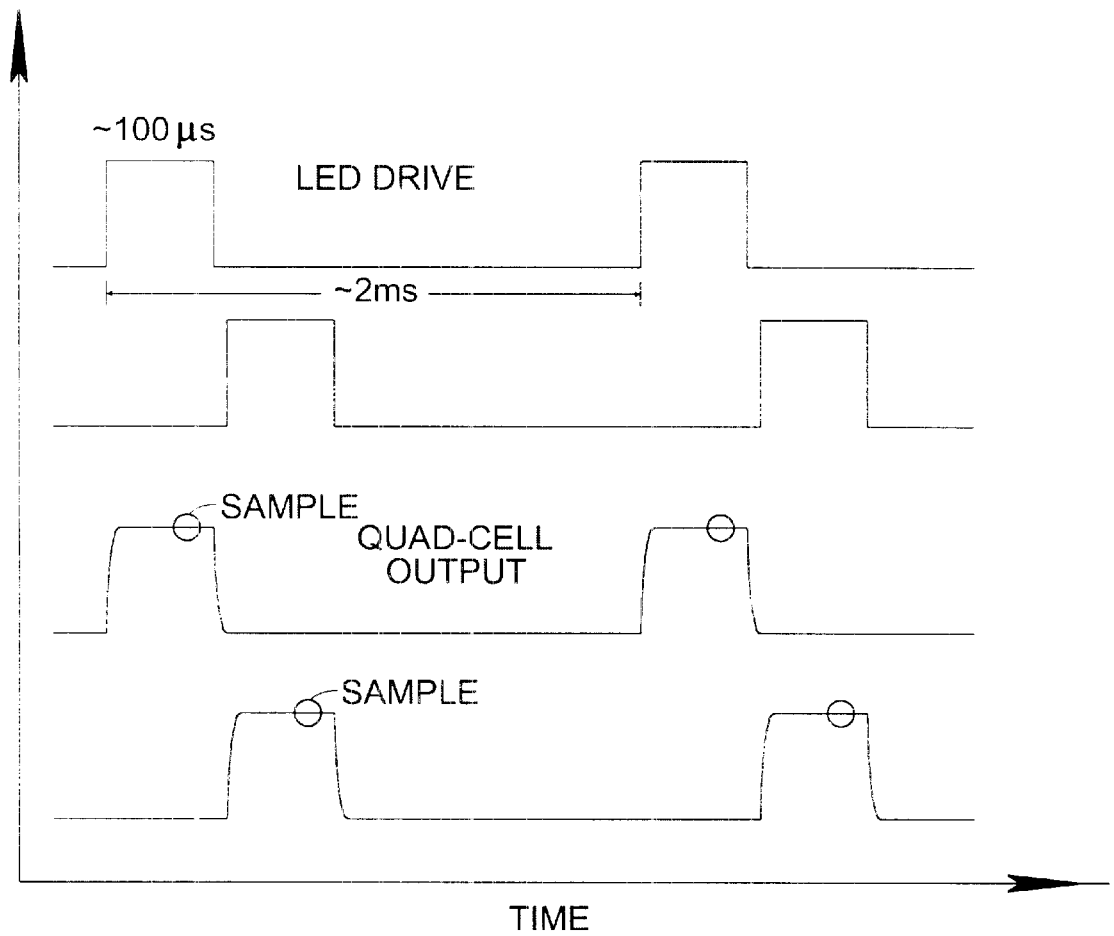
FIG. 7 is an electronic timing diagram relating to illumination and sampling of the quad-cell detector shown in FIG. 6.

In order to avoid interference, provide sufficient illumination intensity, and reduce power consumption, first light source 78A and second light source 78B are illuminated sequentially, and first detector 80A and second detector 80B are sampled sequentially. FIG. 7 is a timing diagram that illustrates that one light source is pulsed for a duration of about 100 µs and then sampled, and then the other light source is pulsed for the same duration and sampled. The cycle is repeated at approximately every 2 ms.

Referring also now to FIG. 8, the analog signals from quadrants Q1–Q4 of detectors 80A, 80B are fed to amplifiers 90 and then input to a sum/difference circuit 92. Sum/difference circuit 92 provides three outputs for each position detector 80A, 80B. Two of the outputs are the respective x and y numerators in the above equations, and the third output is the denominator common to both equations. The output signals are multiplexed by a multiplexor 94 and then provided as analog input to a microprocessor 96, which provides on-board analog-to-digital conversion of the signals. Microprocessor 96 is programmed to calculate the final spot locations $(x_1, y_1)$ and $(x_2, y_2)$.

While the position detection system of the present embodiment is described as employing quad-cell detectors, it is possible to substitute other detector types and configurations for purposes of the present invention. For example, a variety of position sensitive devices (PSDs) are commercially available that can provide local x-y signal information. Also, it is possible to arrange four discrete photosensitive detectors in a quadrant configuration to mimic the quad-cell detector described above.

The global X-Y-Z alignment status of tonometer 10 relative to the eye is then computed by inputting coordinates $x_1, y_1$ from first detector 80A and coordinates $x_2, y_2$ from second detector 80B to a plurality of predetermined geometric relationships stored in programmable memory 98 during calibration of tonometer 10. More specifically, geometrical relationships giving the global position coordinates X, Y, and Z can be determined by multiple regression as follows:

$$X=R_1x_1+R_2y_1+R_3x_2+R_4y_2+R_5,$$

$$Y=R_6x_1+R_7y_1+R_8x_2+R_9y_2+R_{10},$$

and $$Z=R_{11}x_1+R_{12}y_1+R_{13}x_2+R_{14}y_2+R_{15},$$

wherein the regression coefficients $R_1$–$R_{15}$ are found during instrument calibration measurements using an artificial eye.

Figure 9:
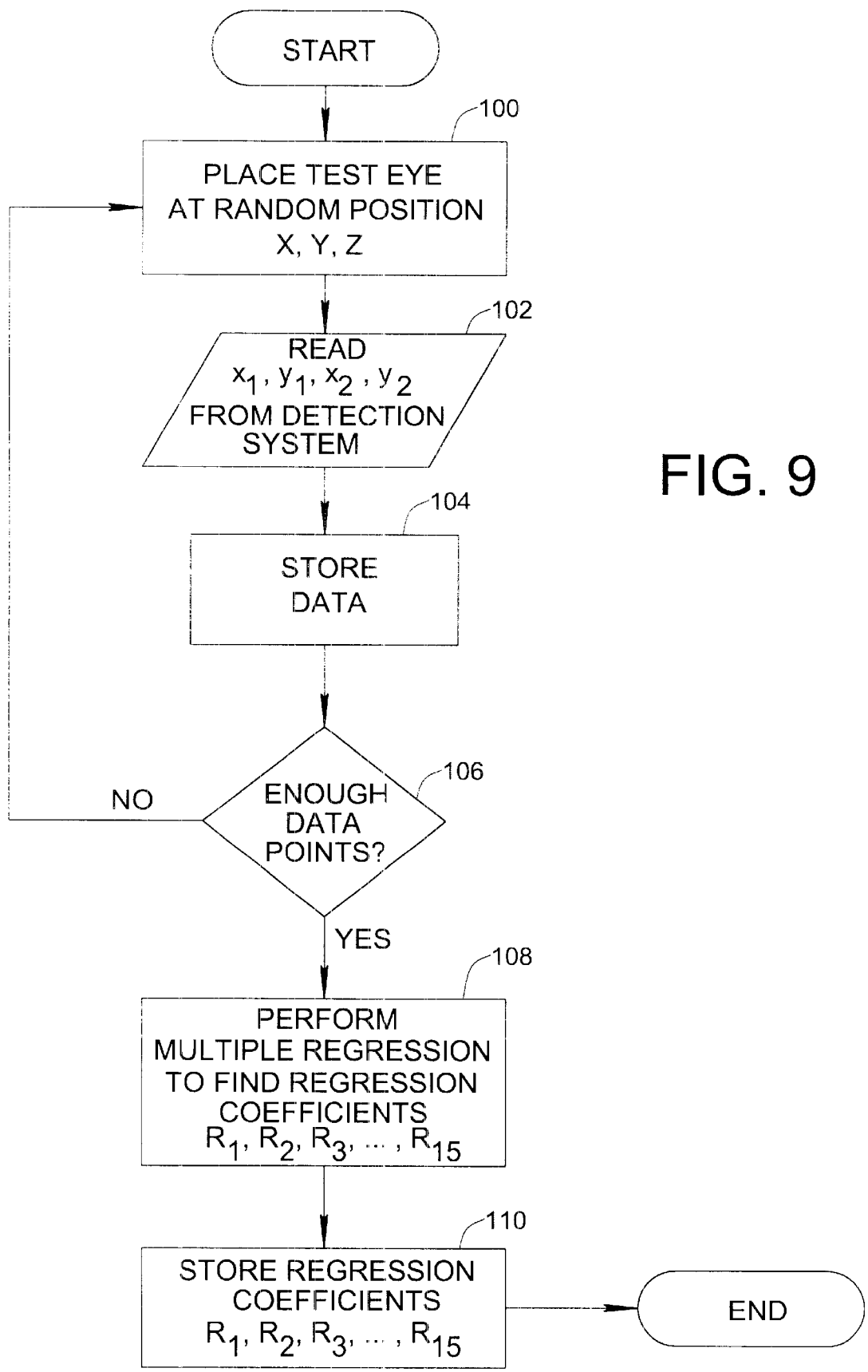
FIG. 9 is a flow diagram of steps followed to calibrate the position detection system shown in FIG. 5.

FIG. 9 is a flow diagram showing the steps followed to calibrate the position detection system of the present invention. First, according to step 100, an artificial "test" eye is placed at a random, known position X, Y, Z relative to tonometer 10. Then, as indicated by steps 102 and 104, the local spot positions $(x_1, y_1)$ and $(x_2, y_2)$ are read from the position detection system and stored in a table with the corresponding known global coordinates X, Y, Z. If a sufficient number of data points have been measured according to query 106, multiple regression is performed in step 108 to find the regression coefficients $R_1$–$R_{15}$, which are then stored in memory pursuant to step 110. If more data points are needed according to query 106, the process returns to step 100 and is repeated. It is preferable to calibrate the position detection system using a large number of random locations of the artificial eye, as this will provide greater accuracy in the determination of the regression coefficients, and ultimately provide improved accuracy in the computed X, Y, Z location of a patient's eye.

The position detection system described above is preferred because it provides X-Y-Z alignment status information at a much higher repetition rate than systems of the prior art, an advantage that is particularly useful for alignment of hand-held instruments. Moreover, the position detection system of the present invention can be calibrated periodically by manufacturer personnel to ensure alignment accuracy. Because of the power demands associated with the preferred position detection system, the position detection system is programmed to operate in two different modes depending upon whether it senses the presence of an eye within a proximity zone or volume just in front of discharge tube 50. When the total illumination optical power received by quadrants Q1–Q4 of detectors 80A, 80B is at a level that indicates the presence of an illumination spot 88 on the corresponding detector, the tonometer is roughly aligned with respect to the eye such that the detectors are receiving corneally reflected light, an indication that the eye is within the proximity zone defined by the orientation and characteristics of the position detection system elements. In this condition, the position detection system operates in a regular mode to provide updated position information at a high frequency, for example every 2 milliseconds. When the signal levels from detectors 80A, 80B fall below a threshold indicating that no eye is present within the proximity zone, the position detection system is switched to an energy-saving mode wherein position signal information is updated at a much lower frequency, for example every two seconds. This feature reduces power consumption to extend the charge life of power source 32.

Figure 10:
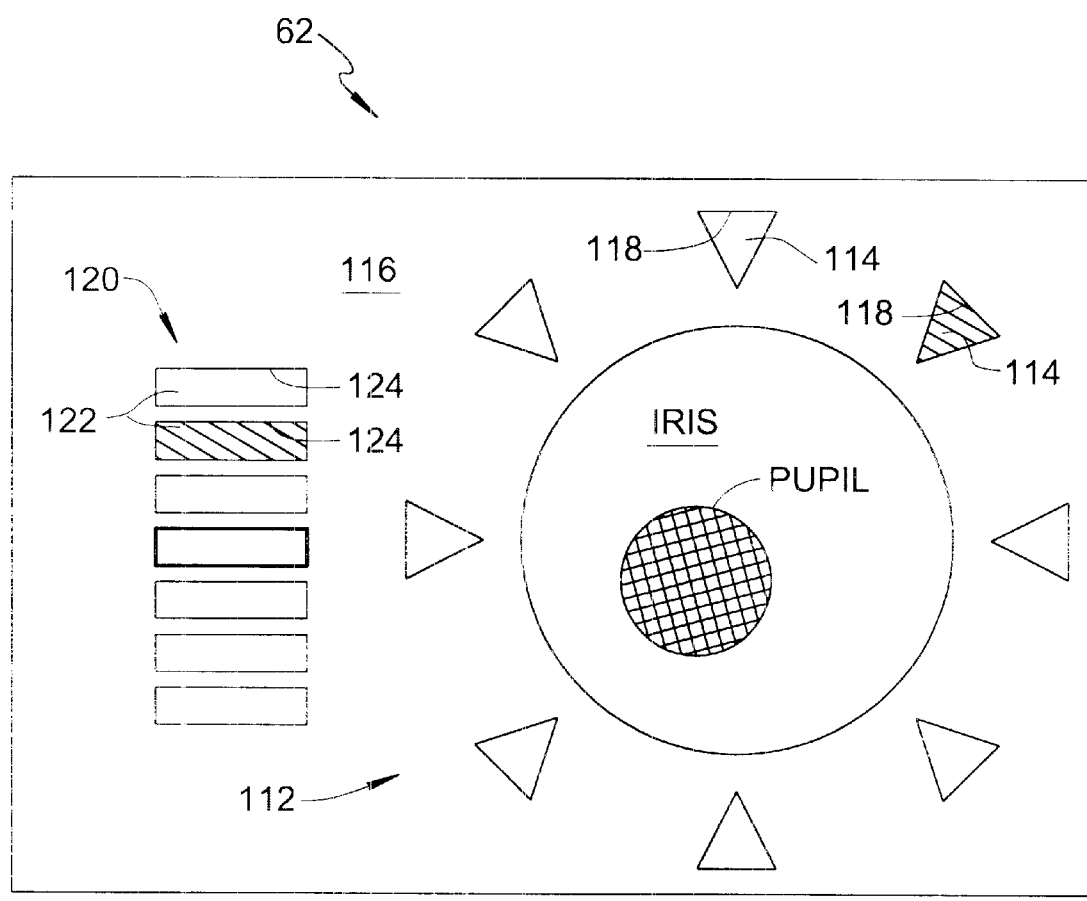
FIG. 10 is an enlarged view of a heads-up display forming part of an alignment system of the hand-held non-contact tonometer shown in FIG. 1.

FIG. 10 shows an enlarged view of "heads-up" display 62 of tonometer 10 as it appears to an operator viewing through eyepiece 18 along optical axis OA. Display 62 assists the operator in aligning the instrument by presenting the computed X-Y-Z alignment status information in a format that instructs the operator regarding movement of the instrument necessary to achieve alignment. Heads-up display 62 comprises a polar array 112 of light-emitting diodes 114 masked by an overlay 116 having light-transmitting directional pointers 118 for providing an X-Y alignment instruction to the operator. The LEDs 114 in polar array 112 are each connected to microprocessor 96 by way of an I$^2$C line 97 and a serial-to-parallel converter (not shown), whereby the LEDs are selectively illuminated depending upon the X-Y alignment status of the instrument relative to the eye. In particular, an LED 114 is illuminated corresponding to an appropriate directional pointer instructing the operator of the direction to move the instrument to align optical axis OA with corneal vertex V. When X-Y alignment is achieved, all the LEDs 114 in polar array 112 can be illuminated in continuous or pulsing fashion to communicate a condition of X-Y alignment to the operator. Heads-up display 62 further comprises a linear array 120 of light-emitting diodes 122 positioned to correspond with light-transmitting rectangles 124 in overlay 116 for purposes of Z-axis alignment. The LEDs 122 in linear array 120 are each connected to microprocessor 96 by way of I$^2$C line 97 and a serial-to-parallel converter (not shown), whereby the LEDs are selectively illuminated depending upon the Z alignment status of the instrument relative to the eye. More specifically, and by way of non-limiting example, the top and bottom LEDs in linear array 120 are the same color (red), the middle LED is another color (green), and the LEDs between the top LED and middle LED and between the bottom LED and the middle LED are all yet another color (yellow). When the instrument is too close to the eye, both red LEDs flash as a warning to the operator. The lower red and yellow LEDs indicate the instrument should be moved away from the eye, while the upper red and yellow LEDs indicate the instrument should be moved toward the eye. The green LED indicates that Z-axis alignment is reached. Currently, it is preferred to provide LEDs 114 and 122 on a single circuit board, and to use photographic film to form overlay 116, which may be separated from the LED circuit board by a spacer (not shown).

As can be seen in FIGS. 3 and 4, the actual heads-up display 62 is located in the instrument at a location off of optical axis OA. An image of heads-up display 62 is projected to the operator along optical axis OA by means of mirror 64 and beamsplitter 66. The X-Y polar array 112 is arranged circumferentially about a real image of the patient's eye transmitted through macro-lens 60, whereby the operator can see the pupil and surrounding iris along with superimposed instructional display cues provided by heads-up display 62. For example, in FIG. 10, the operator is being instructed to move the instrument lower and to the left for X-Y alignment, and closer to the patient's eye for Z alignment.

Tonometric Measurement System

Figure 11:
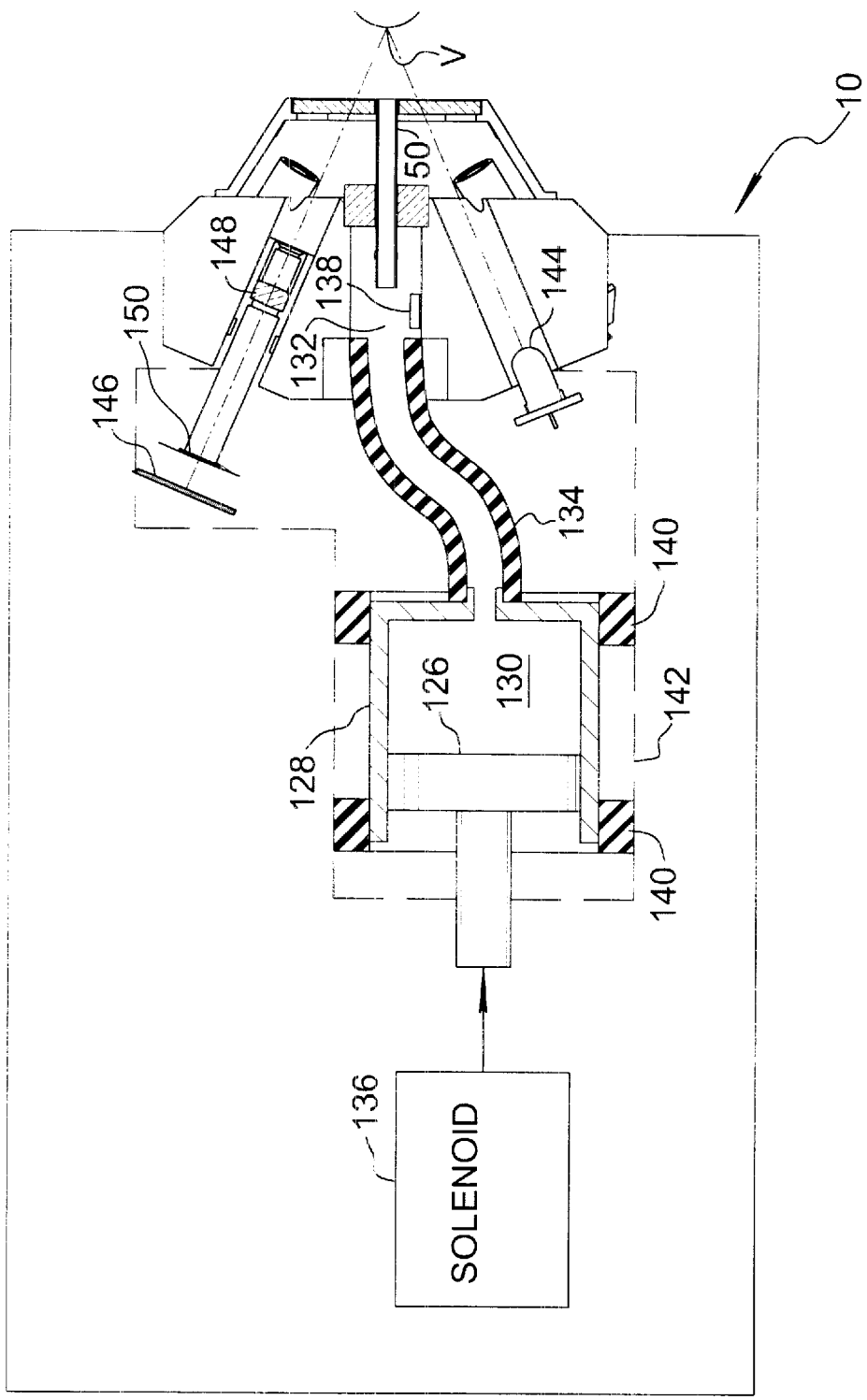
FIG. 11 is a schematic diagram of a fluid pump system of the hand-held non-contact tonometer shown in FIG. 1.

FIG. 11 shows a fluid pump system of tonometer 10 for generating a fluid pulse to deform the patient's cornea. In accordance with a preferred embodiment of the present invention, the fluid pump system comprises a piston 126 axially movable relative to a cylinder 128 for compressing fluid within an internal compression chamber 130 defined thereby, an internal plenum chamber 132 formed in nosepiece 52, a flow tube 134 providing a fluid conduit from compression chamber 130 to plenum chamber 132, and fluid discharge tube 50 extending through and supported by macro-lens 60 and front window 20 for guiding pressurized fluid from plenum chamber 132 along optical axis OA corneal vertex V. A linear solenoid 136 is operatively connected to piston 126 for causing axially directed movement of piston 126 relative to cylinder 128. The linear solenoid 136 is energized by a solenoid drive circuit 137 connected to the solenoid and to microprocessor 96, as shown in FIG. 8.

A pressure sensing device 138, for example a pressure transducer or the like, is located within plenum chamber 132 for generating signal information indicative of the fluid pressure within the plenum chamber. Pressure sensing device 138 is connected to microprocessor 96, which includes an on-board analog-to-digital converter for converting the analog pressure signal to digital form.

A vibration damping material in the construction of flow tube 134 to prevent transmission of vibrations from cylinder 128 to nosepiece 52. Preferably, at least a portion of flow tube 134 is formed of a vibration damping material, such as synthetic rubber, to dissipate vibration energy before it reaches nosepiece 52. In a presently preferred construction, the entire flow tube 134 is formed of polyurethane. Also, at least one vibration damping element 140 operatively arranged between cylinder 128 and support frame 142 for dissipating vibration energy. In an embodiment preferred for its simplicity, a pair of vibration damping elements 140 are configured as rings formed of a vibration damping material fitted circumferentially about cylinder 128 at opposite axial ends thereof. Suitable vibration damping material for forming damping elements 140 is synthetic rubber, for example polyurethane, however other vibration damping materials can be used.

When signal information provided by the position detection system indicates that X-Y-Z alignment exists with respect to the patient's eye, a start signal is transmitted by microprocessor 96 to solenoid drive circuit 137 to automatically energize solenoid 136. As a result, solenoid 136 forces piston 126 to move along its compression stroke and a fluid pulse is expelled through fluid discharge tube 50 toward the eye. As the cornea is deformed, the fluid pressure within plenum chamber 132 is monitored by pressure sensor 138, and the shape of the corneal surface is monitored optically to determine the moment when applanation occurs.

The arrangement for optically detecting applanation is best seen in FIGS. 4 and 11. An infra-red emitter 144 is mounted on nosepiece 52 and obliquely aimed at corneal vertex V, and a photosensitive detector 146 located on the opposite side of optical axis OA and facing corneal vertex V along an oblique direction symmetrically opposite to that of applanation emitter 144. A collector lens 148 and a pinhole diaphragm 150 are located in front of applanation detector 146, which is located in the focal plane of the collector lens. When the cornea is in its normal convex shape, parallel incident rays from emitter 144 are reflected in a fanned-out fashion by the curved corneal surface, and a weak detection signal is generated at applanation detector 146. As a portion of the corneal surface approximates a flat surface at applanation, the incident parallel beam is reflected by the flat surface as a parallel beam in the direction of collector lens 148, which focuses the beam through pinhole diaphragm 150 and onto the surface of applanation detector 146. As a result, applanation detector 146 registers a peak detection signal corresponding to applanation. Those familiar with non-contact tonometers will recognize that this arrangement for optically detecting applanation is already known from the prior art.

The analog signal information from pressure sensor 138 and applanation detector 146 is passed through filter circuits 152 and 154, respectively, and delivered to microprocessor 96, where it is converted to digital form. The detected plenum pressure at the time of applanation is then correlated to IOP.

Wireless Data Exchange

The digital IOP measurement data provided by the tonometric measurement system is uploadable to a remote computer by way of an IRDA transceiver 156 (FIG. 8) located within head portion 16 of housing 12, below nosepiece 52. A corresponding IRDA window (not shown) is provided in housing 12 adjacent to transceiver 156 for transmitting infra-red pulses generated by transceiver 156 and directed to transceiver 156. In this way, wireless data exchange with the remote computer is possible, whereby the operator may export measurement results to a database stored on the remote computer for future reference and analysis.

What is claimed is:

1. A hand-held non-contact tonometer for measuring intraocular pressure of an eye, said tonometer comprising:
   a housing including an elongated handle portion and a head portion connected to said handle portion;
   an opto-electronic tonometric measurement system residing in said head portion of said housing, said tonometric measurement system including an optical axis and a fluid discharge tube aligned on said optical axis, said fluid discharge tube having a fluid exit end;
   a position detection system residing in said head portion of said housing for generating signal information indicative of the XY location of said optical axis relative to a corneal vertex of said eye and the Z location of said exit end of said fluid discharge tube relative to said corneal vertex;

a view path along through said head portion of said housing along said optical axis for enabling an operator to directly view said eye; and a display connected to said position detection system for guiding said operator in achieving XY alignment of said optical axis with said corneal vertex and Z alignment of said exit end of said fluid discharge tube at a predetermined distance from said corneal vertex based on said signal information.

2. The hand-held non-contact tonometer according to claim 1, wherein said handle portion of said housing extends along a handle axis, and said handle axis forms an oblique angle with said optical axis.

3. The hand-held non-contact tonometer according to claim 1, further comprising a D.C. power supply residing in said handle portion of said housing for supplying power to said tonometric measurement system, said position detection system, and said display.

4. The hand-held non-contact tonometer according to claim 3, wherein said position detection system defines a proximity zone, and said position detection system is effective to provide said signal information when said eye is located within said proximity zone.

5. The hand-held non-contact tonometer according to claim 4, wherein said position detection system operates in a regular mode when an eye is detected within said proximity zone and in an energy-saving mode when no eye is detected within said proximity zone.

6. The hand-held non-contact tonometer according to claim 5, wherein said signal information is updated at a higher frequency in said regular mode than in said energy-saving mode.

7. The hand-held non-contact tonometer according to claim 1, further comprising a transceiver for wireless communication of measurement data to a remote computer.

8. The hand-held non-contact tonometer according to claim 7, wherein said transceiver is an IRDA transceiver.

9. The hand-held non-contact tonometer according to claim 1, further comprising a beamsplitter arranged on said optical axis for reflecting an image of said display toward said operator, whereby said image of said display is superimposed with a real image of said eye.

10. In combination:

a hand-held non-contact tonometer comprising:

a housing including a handle portion having a bottom end and an opposite top end, said housing further including a head portion connected to said top end of said handle portion:

a rechargeable D.C. power source residing in said handle portion of said housing;

an opto-electronic tonometric measurement system residing in said head portion of said housing and powered by said D.C. power source; and a stand for supporting said hand-held non-contact tonometer in an upright orientation when said hand-held non-contact tonometer is not in use, said stand including a D.C. power source charger operatively connected to said rechargeable D.C. power source when said tonometer is supported by said stand;

wherein said non-contact tonometer is not freestanding in said upright orientation.

11. The combination according to claim 10, wherein said bottom end of said handle portion defines a curved surface.

* * * * *